(12) United States Patent
Fan

(10) Patent No.: US 12,193,857 B2
(45) Date of Patent: Jan. 14, 2025

(54) SYSTEMS AND METHODS FOR COMPUTED TOMOGRAPHY

(71) Applicant: GE Precision Healthcare LLC, Wauwatosa, WI (US)

(72) Inventor: Jiahua Fan, Waukesha, WI (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 437 days.

(21) Appl. No.: 17/805,831

(22) Filed: Jun. 7, 2022

(65) Prior Publication Data
US 2023/0389883 A1    Dec. 7, 2023

(51) Int. Cl.
*A61B 6/40* (2024.01)
*A61B 6/00* (2024.01)
*A61B 6/03* (2006.01)
*A61B 6/42* (2024.01)

(52) U.S. Cl.
CPC .............. *A61B 6/405* (2013.01); *A61B 6/032* (2013.01); *A61B 6/4241* (2013.01); *A61B 6/542* (2013.01)

(58) Field of Classification Search
CPC ....... A61B 6/405; A61B 6/032; A61B 6/4241; A61B 6/542; G01T 1/2964; G01T 1/24
See application file for complete search history.

(56) References Cited

U.S. PATENT DOCUMENTS

| | | |
|---|---|---|
| 7,696,483 B2 | 4/2010 | Tkaczyk et al. |
| 9,952,164 B2 | 4/2018 | Wiedmann |
| 10,085,698 B2 | 10/2018 | Fan et al. |
| 10,383,585 B2 * | 8/2019 | Konno ................. A61B 6/4241 |
| 11,344,266 B2 * | 5/2022 | Iniewski ................... G01T 1/24 |

FOREIGN PATENT DOCUMENTS

JP    2009018154 A    1/2009

OTHER PUBLICATIONS

EP application 23174475.6 filed May 22, 2023—extended Search Report issued Nov. 8, 2023; 7 pages.
JP 2009-018154 English Abstract; Espacenet search Feb. 6, 2024; 1 page.

* cited by examiner

*Primary Examiner* — David P Porta
*Assistant Examiner* — Meenakshi S Sahu
(74) *Attorney, Agent, or Firm* — McCoy Russell LLP

(57) ABSTRACT

Methods and systems are provided for increasing a quality of computed tomography (CT) images. In one embodiment, a method for a photon-counting computed tomography (PCCT) system comprises, adjusting an X-ray tube output current of the PCCT system across and/or within one or more views, the current adjusted between a first current and a second current, the first current higher than the second current; for a view of the one or more views scanned by the PCCT system, applying a first pile-up correction to a first photon count output at each detector of a detector array of the PCCT system at the first current, the first pile-up correction calculated based on a second pile-up correction applied to a second photon count output at each detector at the second current; and reconstructing an image based on the corrected first photon count and the corrected second photon count.

20 Claims, 9 Drawing Sheets

SYSTEMS AND METHODS FOR COMPUTED TOMOGRAPHY

TECHNICAL FIELD

Embodiments of the subject matter disclosed herein relate to imaging systems and methods, and more particularly, to automated current modulation in computerized tomography (CT) imaging systems.

BACKGROUND

In computed tomography (CT) imaging systems, an electron beam generated by a cathode is directed towards a target within an X-ray tube. A fan-shaped or cone-shaped beam of X-rays produced by electrons colliding with the target is directed towards a subject, such as a patient. After being attenuated by the object, the X-rays impinge upon an array of X-ray detectors, generating an image. A quality of a CT image may be increased by using Photon Counting CT (PCCT), where the X-ray detectors are photon-counting detectors, and photons are counted to provide spectral information. Automatic Exposure Control (AEC) may be used in conjunction with PCCT, where X-ray tube output current is adjusted view by view to minimize a dosage of radiation applied to the patient while maintaining constant image quality across a scan range of the patient.

However, with a PCCT system, photon pile-up may occur at higher input count rates due to a limited capability of the photon-counting detectors. As a result, an output of the photon-counting detectors must be corrected for pile-up effects. Correcting for different amounts of pile-up may be difficult to perform accurately. The pile-up may occur at different detectors depending on a size and density of an anatomical region being scanned. For example, when a high amount of current is applied when scanning a patient, pile-up may not occur at detectors receiving X-ray beams that are attenuated by the patient, and pile up may occur at detectors receiving X-ray beams that are not attenuated by the patient (e.g., through narrow parts or around skin lines of the patient). As a result, applying a pile-up correction across a plurality of the different detectors may produce inconsistent results, reducing a quality of images acquired by the PCCT system.

SUMMARY

The current disclosure at least partially addresses one or more of the above identified issues by a method for a photon-counting computed tomography (PCCT) system, the method comprising, during a scan of a subject, adjusting an X-ray tube output current of the PCCT system across and/or within one or more views, the current adjusted between a first current and a second current, the first current higher than the second current; for a view of the one or more views scanned by the PCCT system, applying a first pile-up correction to a first photon count output at each detector of a detector array of the PCCT system at the first current, the first pile-up correction calculated based on a second pile-up correction applied to a second photon count output at each detector at the second current; and reconstructing an image based on the corrected first photon count and the corrected second photon count, and outputting the image to a display device of the PCCT system. In this way, a pile-up correction calculated for a detector at a lower photon count may be used to guide a pile-up correction at the detector for a higher photon count, and an image may be reconstructed based on each corrected photon count. Because pile-up behavior becomes harder to compensate for as a rate of incoming photons increases, by using the pile-up correction calculated at the lower photon count to correct for pile-up where the photon count is higher, a quality of the reconstructed image may be increased.

In some examples, the first, higher current may be applied in a first view, the second, lower current may be applied in a second view, and a first pile-up correction calculated for each detector in the second view may be used to guide a second pile-up correction calculated for each detector in the first view (e.g., view-to-view current modulation). In other examples, the first, higher current may be applied in a first portion of a view, the second, lower current may be applied in a second portion of the view, and a first pile-up correction calculated for calculated for each detector in the second portion may be used to guide a second pile-up correction of calculated for each detector in the first portion (e.g., intra-view current modulation). Corrected photon counts for each detector in the first portion and the second portion of the view may then be summed to generate a total photon count for each detector for the view. In yet other examples, view-to-view current modulation and intra-view current modulation may be combined to increase an accuracy of pile-up corrections, and a quality of a resulting reconstructed image.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which.

Figure 1:
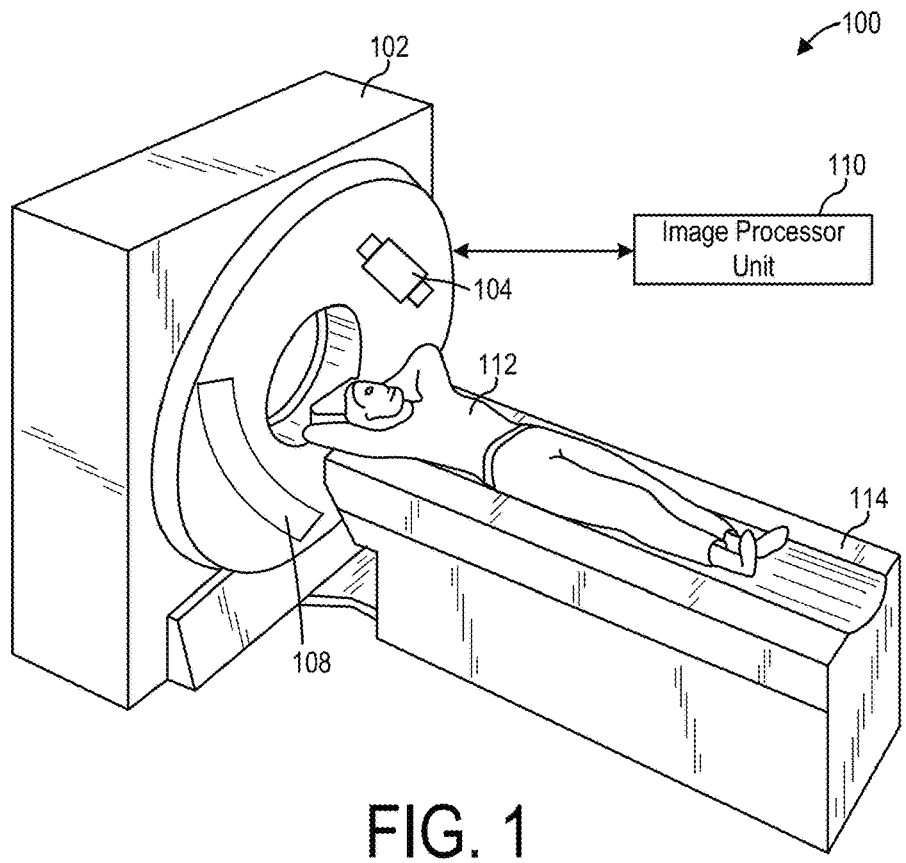
FIG. 1 shows a pictorial view of a computed tomography (CT) imaging system, in accordance with one or more embodiments of the present disclosure.

The drawings illustrate specific aspects of the described systems and methods. Together with the following description, the drawings demonstrate and explain the structures, methods, and principles described herein. In the drawings, the size of components may be exaggerated or otherwise modified for clarity. Well-known structures, materials, or operations are not shown or described in detail to avoid obscuring aspects of the described components, systems and methods.

DETAILED DESCRIPTION

This description and embodiments of the subject matter disclosed herein relate to methods and systems for increasing a quality of images acquired via a photon-counting computed tomography (PCCT) system. Typically, in computed tomography (CT) imaging systems, an X-ray source or X-ray tube emits a fan-shaped beam or a cone-shaped beam towards an object, such as a patient. Generally, in CT systems the X-ray source and the detector array are rotated about a gantry within an imaging plane and around the patient, and images are generated from projection data at a plurality of views at different view angles. For example, for one rotation of the X-ray source, 1000 views may be generated by the CT system. The beam, after being attenuated by the patient, impinges upon an array of radiation detectors. The X-ray detector or detector array typically includes a collimator for collimating X-ray beams received at the detector, a scintillator disposed adjacent to the collimator for converting X-rays to light energy, and photodiodes for receiving the light energy from the adjacent scintillator and producing electrical signals therefrom. An intensity of the attenuated X-ray beam radiation received at the detector array is typically dependent upon the attenuation of the X-ray beam by the patient. Each detector element of a detector array produces a separate electrical signal indicative of the attenuated beam received by each detector element. The electrical signals are transmitted to a data processing system for analysis. The data processing system processes the electrical signals to facilitate generation of an image.

Such conventional CT imaging systems utilize detectors that convert radiographic energy into current signals that are integrated over a time period, then measured and ultimately digitized. However, a drawback of such detectors is their inability to provide data or feedback as to the number and/or energy of photons detected. That is, the light emitted by the scintillator is a function of both a number of X-rays impinged and an energy level of the X-rays. The photodiodes may not be capable of discriminating between the energy level or the photon count from the scintillation. For example, two scintillators may illuminate with equivalent intensity and, as such, provide equivalent output to their respective photodiodes. Yet, despite yielding an equivalent light output, the number of X-rays received by each scintillator may be different, and an intensity of the X-rays may be different.

In contrast, PCCT detectors may provide photon counting and/or energy discriminating feedback with high spatial resolution. PCCT detectors can be caused to operate in an X-ray counting mode, an energy measurement mode of each X-ray event, or both. While a number of materials may be used in the construction of a direct conversion energy discriminating detector, semiconductors have been shown to be one preferred material. Typical materials for such use includes Cadmium Zinc Telluride (CZT), Cadmium Telluride (CdTe) and Silicon (Si), which have a plurality of pixilated anodes at attached thereto.

A drawback of direct conversion semiconductor detectors, however, is that these types of detectors cannot count at the X-ray photon fluxes typically encountered with conventional CT systems. Saturation can occur at detector locations wherein small subject thickness is interposed between the X-ray detector and the X-ray source or X-ray tube. These saturated regions correspond to paths of low subject thickness near or outside the width of the subject projected onto the detector fan-arc. In many instances, the subject is more or less circular or elliptical in the effect on attenuation of the X-ray flux and subsequent incident intensity to the detector. In this case, the saturated regions represent two disjointed regions at extremes of the fan-arc. In other less typical, but not rare instances, saturation occurs at other locations and in more than two disjointed regions of the detector.

In the case of an elliptical subject, the saturation at the edges of the fan-arc may be reduced by the imposition of a bowtie filter between the subject and the X-ray source. The filter may be constructed to match the shape of the subject in such a way as to equalize total attenuation, filter and subject, across the fan-arc. The flux incident to the detector is then relatively uniform across the fan-arc and does not result in saturation. However, the bowtie filter may not be optimal given that a subject population is significantly less than uniform and not exactly elliptical in shape. In such cases, it is possible for one or more disjointed regions of saturation to occur or conversely to over-filter the X-ray flux and create regions of very low flux. Low X-ray flux in the projection will ultimately contribute to noise and artifacts in the reconstructed image of the subject.

"Pile-up" is a phenomenon that occurs when a source flux at the detector is so high that there is a non-negligible possibility that two or more X-ray photons deposit charge packets in a single pixel close enough in time so that their signals interfere with each other. Pile-up phenomenon are of two general types, which result in somewhat different effects. In the first type, the two or more events are separated by sufficient time so that they are recognized as distinct events, but the signals overlap so that the precision of the measurement of the energy of the later arriving X-ray or X-rays is degraded. This type of pile-up results in a degradation of the energy resolution of the system. In the second type of pile-up, the two or more events arrive close enough in time so that the system is not able to resolve them as distinct events. In such a case, these events are recognized as one single event having the sum of their energies and the events are shifted in the spectrum to higher energies. In addition, pile-up leads to a more or less pronounced depression of counts in high X-ray flux, resulting in detector quantum efficiency (DQE) loss.

This pile-up may lead to detector saturation, which occurs at relatively low X-ray flux level thresholds in direct conversion sensors. Above these thresholds, the detector response is not predictable and has degraded dose utilization that leads to loss of imaging information and results in noise and artifacts in X-ray projection and CT images. In particular, photon counting, direct conversion detectors saturate due to the intrinsic charge collection time (i.e., dead time) associated with each X-ray photon event. Saturation will occur due to pulse pile-up when X-ray photon absorption rate for each pixel is on the order of the inverse of this charge collection time.

PCCT systems typically have one or more energy bins that are determined by a comparator that typically is part of a readout of a data acquisition system (DAS). For a one-bin system, typically one energy threshold of the comparator is set to an energy value that is high enough such that there are few or no false noise counts, but low enough such that there is little loss of signal X-rays in the readout process. Such a system is subject to statistical error and bias due to the pile-up of multiple energy events, as described.

A system having many energy bins may be formed with multiple comparators in the readout DAS. Each comparator may be set to trigger for photons above a set level of energy that results in accumulation on a register of the number of photons above a corresponding X-ray energy level. The bin counts may be weighted and added together to form a system output having specific information content appropriate for an imaging system. However, like a one-bin system, a multiple bin system is subject to degradation due to pile-up, resulting in DQE loss.

PCCT systems may rely on Automatic Exposure Control (AEC) to maintain constant image quality across a scan range of the patient while minimizing a radiation dose applied to the patient. With AEC, for a specific clinical task, based on certain pre-defined image quality metric, X-ray tube output current is adjusted view by view. That is, higher or lower current may be applied for each individual imaging view based on demands of the clinical task. Typically, pile-up behavior must be corrected for when developing a current modulation design for adjusting current across different views. The larger an incoming photon rate, the higher the pile-up behavior, where output photon counts collected from piled up detectors will not follow a linear relation with respect to input photon counts generated by the X-ray source. A quality of acquired images may therefore depend on an accuracy of the current modulation design, which in turn may depend on an accuracy of the pile-up correction.

However, the accuracy of the pile-up correction may depend on the pile-up behavior itself, where a pile-up correction for a lower amount of pile-up may be more accurate than a pile-up correction for a higher amount of pile-up. As a result, a pile-up correction that is applied equally to detectors experiencing a higher amount of pile-up and detectors experiencing a lower amount of pile-up may not accurately compensate for pile-up at either the high pile-up detectors or the low pile-up detectors.

Thus, systems and methods are proposed herein that incorporate pile-up compensation into an AEC modulation, using different current waveforms in a manner that uses a pile-up correction for lower pile-up measurements to guide a pile-up correction for higher pile-up measurements. Because it is easier to accurately correct for lower amounts of pile-up than higher amounts of pile-up, using the pile-up correction for the lower pile-up measurements to guide the pile-up correction for the higher pile-up measurements may increase an overall pile-up correction accuracy. Based on the AEC design scheme and correction algorithm applied, more linear photon counts may be provided with respect to a full current range. Thus, an image quality target from AEC may be better achieved.

Figure 2:
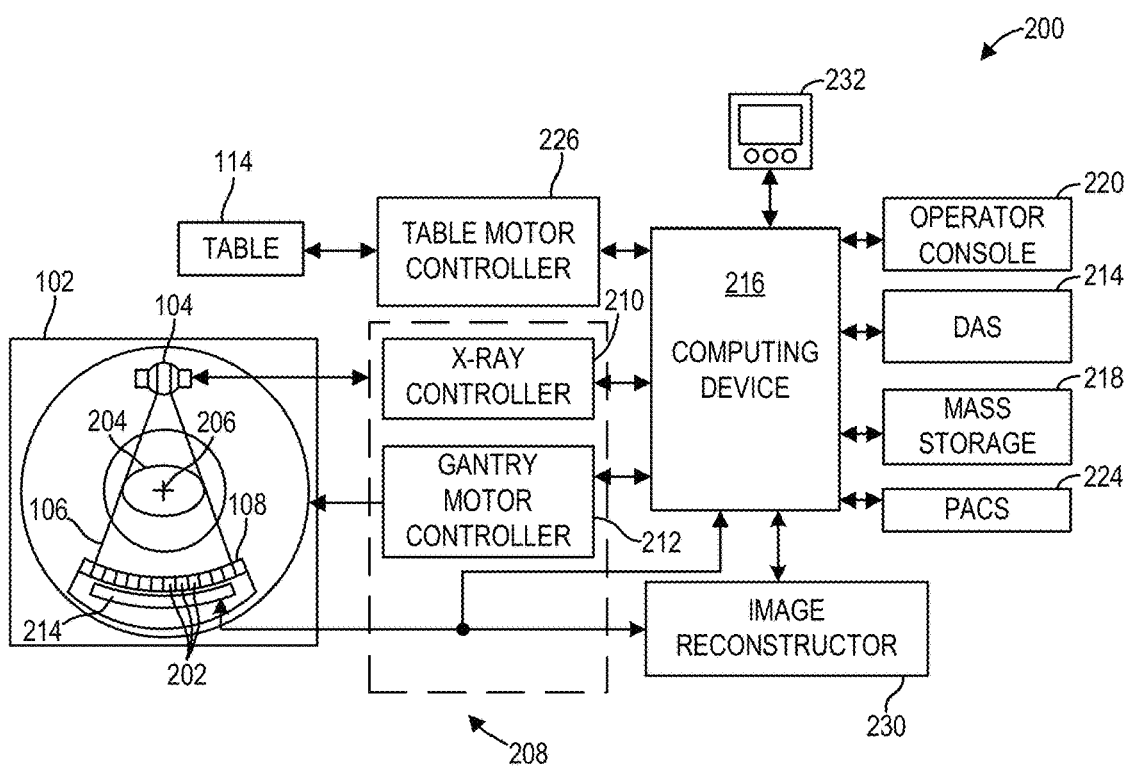
FIG. 2 shows a block schematic diagram of an example CT imaging system, in accordance with one or more embodiments of the present disclosure.
Figure 3:
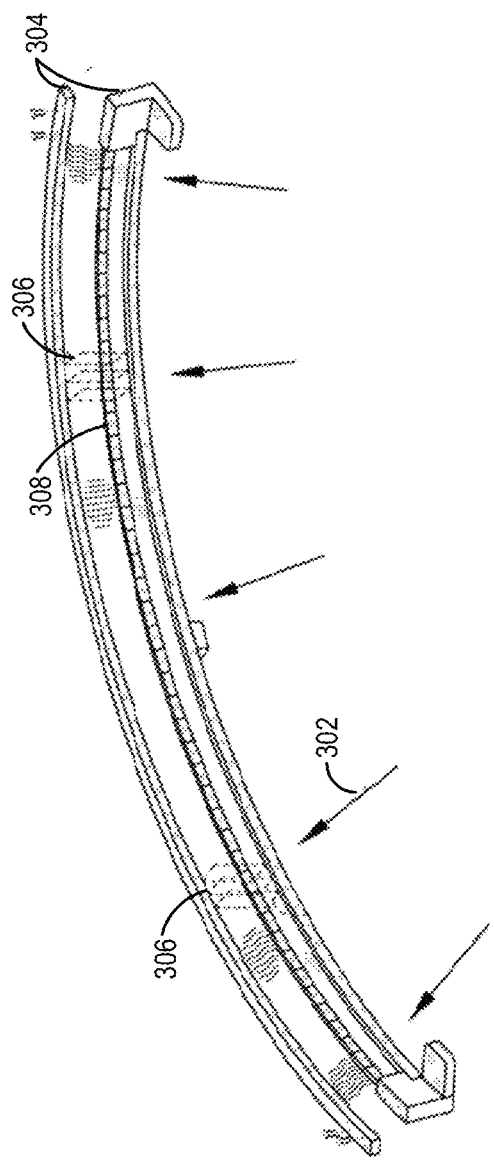
FIG. 3 is a schematic diagram of an exemplary detector array of a PCCT system, in accordance with one or more embodiments of the present disclosure.

An example of a PCCT system that may be used to perform contrast scans in accordance with the present techniques is provided in FIGS. 1 and 2. FIG. 3 shows an example detector array of the PCCT system, where photons of X-rays directed at a subject by an X-ray source are counted by detectors of the detector array. Pile-up in photon counts may occur at the detectors, where pile-up behavior may be different at different detectors, as described in reference to FIG. 4. FIG. 5 shows a graph with exemplary pile-up behavior, where output photon counts diverge from a linear relationship with input photon counts, generating a pile-up curve. A pile-up correction may be applied to a readout from photon-counting detectors of a PCCT system by following one or more steps of a method shown in FIG. 7. To correct the pile-up behavior, current may be modulated across views of the PCCT system in accordance with a function that includes a characterization of the pile-up behavior, by following one or more steps of the method of FIG. 8. The current may also be modulated within a view, where a low current may be used during scanning of a first portion of the view, and a high current may be used during scanning of a second portion of the view, and resulting output photon counts may be averaged to generate corrected output counts, as shown graphically in FIG. 6 and described in reference to the method of FIG. 9. By correcting for the pile-ups as described herein, an error rate in photon counts may be reduced, as described in relation to the examples shown in FIGS. 10A and 10B.

FIG. 1 illustrates an exemplary PCCT system 100 configured for CT imaging with photon-counting detectors. Particularly, the PCCT system 100 is configured to image a subject 112 such as a patient, an inanimate object, one or more manufactured parts, and/or foreign objects such as dental implants, stents, and/or contrast agents present within the body. In one embodiment, the PCCT system 100 includes a gantry 102, which in turn, may further include at least one X-ray source 104 configured to project a beam of X-ray radiation 106 (see FIG. 2) for use in imaging the subject 112 laying on a table 114. Specifically, the X-ray source 104 is configured to project the X-ray radiation beams 106 towards a detector array 108 positioned on the opposite side of the gantry 102. Although FIG. 1 depicts a single X-ray source 104, in certain embodiments, multiple X-ray sources and detectors may be employed to project a plurality of X-ray radiation beams for acquiring projection data at different energy levels corresponding to the patient. In some embodiments, the X-ray source 104 may enable dual-energy gemstone spectral imaging (GSI) by rapid peak kilovoltage (kVp) switching. In the embodiments described herein, the X-ray detector employed is a photon-counting detector which is capable of differentiating X-ray photons of different energies.

In certain embodiments, the PCCT system 100 further includes an image processor unit 110 configured to reconstruct images of a target volume of the subject 112 using an iterative or analytic image reconstruction method. For example, the image processor unit 110 may use an analytic image reconstruction approach such as filtered back projection (FBP) to reconstruct images of a target volume of the patient. As another example, the image processor unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112. As described further herein, in some examples the image processor unit 110 may use both an analytic image reconstruction approach such as FBP in addition to an iterative image reconstruction approach.

In some CT imaging system configurations, an X-ray source projects a cone-shaped X-ray radiation beam which is collimated to lie within an X-Y-Z plane of a Cartesian coordinate system and generally referred to as an "imaging plane." The X-ray radiation beam passes through an object being imaged, such as the patient or subject. The X-ray radiation beam, after being attenuated by the object, impinges upon an array of detector elements. The intensity of the attenuated X-ray radiation beam received at the detector array is dependent upon the attenuation of an X-ray radiation beam by the object. Each detector element of the array produces a separate electrical signal that is a measurement of the X-ray beam attenuation at the detector location. The attenuation measurements from all the detector elements are acquired separately to produce a transmission profile.

In some CT systems, the X-ray source and the detector array are rotated with a gantry within the imaging plane and around the object to be imaged such that an angle at which the X-ray beam intersects the object constantly changes. A group of X-ray radiation attenuation measurements, e.g., projection data, from the detector array at one gantry angle is referred to as a "view." A "scan" of the object includes a set of views made at different gantry angles, or view angles, during one revolution of the X-ray source and detector.

FIG. 2 illustrates an exemplary imaging system 200 similar to the PCCT system 100 of FIG. 1. In accordance with aspects of the present disclosure, the imaging system 200 is configured for imaging a subject 204 (e.g., the subject 112 of FIG. 1). In one embodiment, the imaging system 200 includes the detector array 108 (see FIG. 1). The detector array 108 further includes a plurality of detector elements 202 that together sense the X-ray radiation beam 106 (see FIG. 2) that pass through the subject 204 (such as a patient) to acquire corresponding projection data. In some embodiments, the detector array 108 may be fabricated in a multi-slice configuration including the plurality of rows of cells or detector elements 202, where one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the X-ray source 104 and the detector array 108 rotate, the detector array 108 collects data of the attenuated X-ray beams. The data collected by the detector array 108 undergoes pre-processing and calibration to condition the data to represent the line integrals of the attenuation coefficients of the scanned subject 204. The processed data are commonly called projections. In some examples, the individual detectors or detector elements 202 of the detector array 108 may include photon-counting detectors which register the interactions of individual photons into one or more energy bins.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a 3D volumetric image of the basis material, for example, bone, soft tissue, and/or contrast agent, in the imaged volume.

Once reconstructed, the basis material image produced by the imaging system 200 reveals internal features of the subject 204, expressed in the densities of two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the X-ray source 104. In certain embodiments, the control mechanism 208 further includes an X-ray controller 210 configured to provide power and timing signals to the X-ray source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The DAS 214 may be further configured to selectively aggregate analog data from a subset of the detector elements 202 into so-called macro-detectors, as described further herein. The data sampled and digitized by the DAS 214 is transmitted to a computer or computing device 216. In one example, the computing device 216 stores the data in a storage device or mass storage 218. The storage device 218, for example, may be any type of non-transitory memory and may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the X-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates one operator console 220, more than one operator console may be coupled to the imaging system 200, for example, for inputting or outputting system parameters, requesting examinations, plotting data, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the imaging system 200 either includes, or is coupled to, a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 114 which may be a motorized table. Specifically, the table motor controller 226 may move the table 114 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized X-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 may transmit the reconstructed images to the computing device 216 for generating useful patient information for diagnosis and evaluation. In certain embodiments, the computing device 216 may transmit the reconstructed images and/or the patient information to a display or display device 232 communicatively coupled to the computing device 216 and/or the image reconstructor 230. In some embodiments, the reconstructed images may be transmitted from the computing device 216 or the image reconstructor 230 to the storage device 218 for short-term or long-term storage.

Referring now to FIG. 3, a PCCT photon-counting detector array 300 is shown, which may be a non-limiting example of detector array 108 of FIG. 2. Detector array 300 includes rails 304 having collimating blades or plates 306 placed therebetween. Plates 306 are positioned to collimate X-rays 302 before such beams impinge upon a plurality of detectors 308 of detector array 300, which may be arranged between the plates 306. As an example, detector array 300 may include 57 detectors 308, each detector 308 having an array size of 64×16 of pixel elements. As a result, detector array 300 would have 64 rows and 912 columns (16×57 detectors), allowing for 64 simultaneous slices of data to be collected with each gantry rotation (e.g., the gantry 102 of FIG. 1).

As described above, each detector 308 may be designed to directly convert radiographic energy to electrical signals containing energy discriminatory or photon count data. However, during a pile-up event, two incoming photons may simultaneously, or nearly simultaneously, impinge upon a detector 308 during the readout period of the electronics. During such an event, a combined energy of the two photons may exceed a maximum photon energy level of the incoming spectrum for a single photon. Accordingly, a charge may be generated within a semiconductor layer of the detector 308 that exceeds reference voltages. Thus, counts made at the detector 308 may be incremented.

Figure 4:
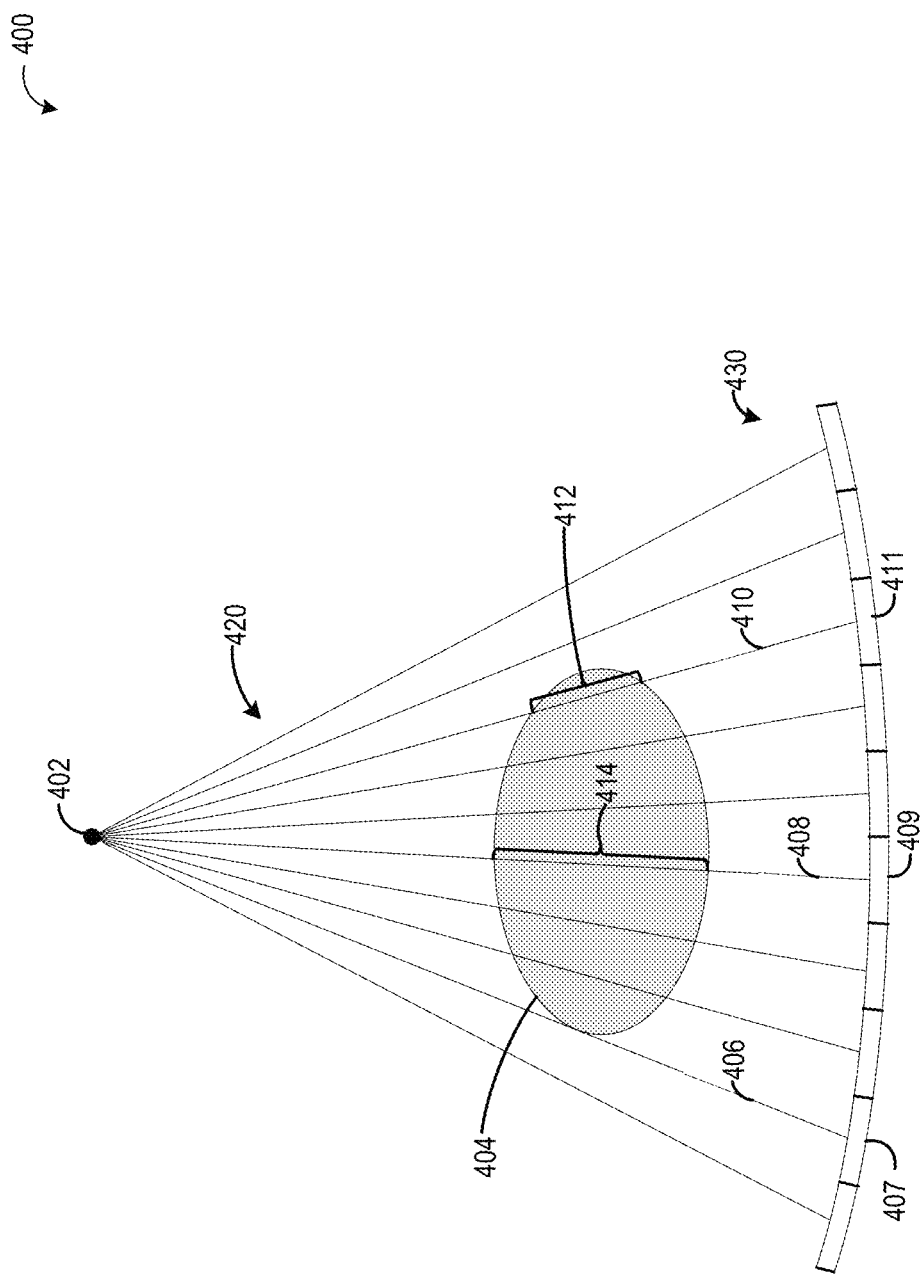
FIG. 4 shows rays of a PCCT system directed at photon-counting detectors during scanning of a subject, in accordance with one or more embodiments of the present disclosure.
Figure 5:
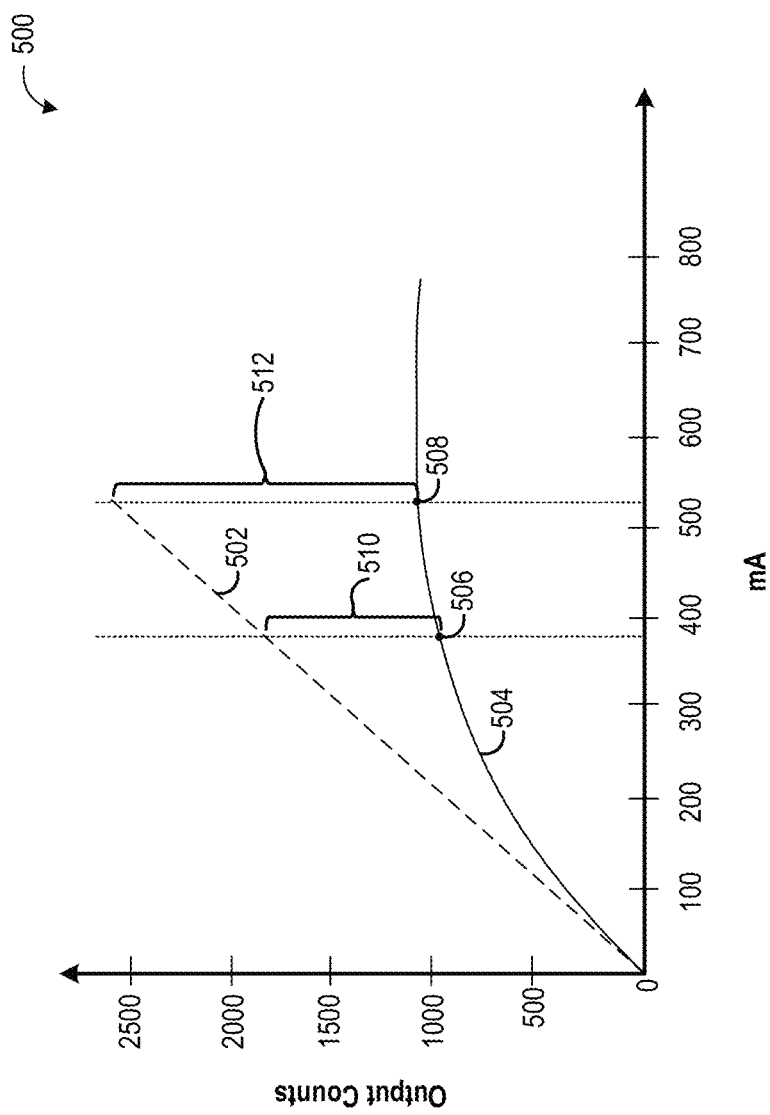
FIG. 5 shows a graph illustrating a photon pile-up curve, in accordance with one or more embodiments of the present disclosure.

FIG. 4 shows a single acquisition view 400 of a subject 404 (e.g., a patient) by an X-Ray source 402 of a PCCT system. The X-ray source 402 and subject 404 may be non-limiting examples of X-ray source 104 and subjects 112, 204 of PCCT system 100 and/or imaging system 200 of FIGS. 1 and 2. FIG. 4 shows a plurality of X-rays 420 generated by the X-ray source 402, which impinge on a plurality of photon-counting detectors of a detector array 430 (e.g., detector array 108 of FIG. 2). For example a first X-ray 406 impinges on a first detector 407; a second X-ray 408 impinges on a second detector 409; and a third X-ray 410 impinges on a third detector 411.

Because of a limited capability of the photon-counting detectors, pile-up is a significant issue one needs to correct for PCCT, especially when a flux of the X-rays is high. The flux may be high when the X-rays are generated as a result of a high current being delivered to the X-ray source, for example, during an AEC scheme where high current is used. When a high current is applied when a subject is being scanned, a high percentage of X-rays striking the subject may be attenuated by the subject. As a result, photon counts at detectors behind the subject may not be high, and pile-up may not be an issue. However, for X-rays going through a narrow part of the subject, and/or X-rays around skin lines of the subject, photon counts may be high, where pile-up may be an issue.

For example, in FIG. 4, a high current may be applied to the X-ray source 402, generating a high flux in the X-rays 420. The first X-ray 406 passes by a side of the subject 404 before impinging on the first detector 407. As a result of passing by a side of the subject 404, a first photon count at the first detector 407 may be high, where pile-up may be an issue at the first detector 407. The second X-ray 408 passes through a thick portion 414 of the subject 404 before impinging on the second detector 409. For example, the thick portion 414 may include dense portions of the subject 404, such as bone or areas permeated by a contrast agent. As a result of passing through the thick portion 414 of subject 404, a second photon count at the second detector 409 may be low, as a result of a portion of the photons of second x-ray 408 being attenuated by the subject 404. As a result of the second photon count being low, pile-up may not be an issue at the second detector 409.

The third X-ray 410 passes through a narrow portion 412 of the subject 404, before impinging on the third detector 411. The narrow portion 412 may not include dense portions of the subject 404. For example, the narrow portion 412 may include skin and muscle tissue of the subject 404, and/or areas not permeated by a contrast agent. As a result of the third X-ray 410 passing through the narrow portion 412 of the subject 404, a third photon count at the third detector 411 may be lower than the second photon count at second detector 409, and higher than the first photon count at first detector 407. As a result of the third photon count being lower than the second photon count, pile-up at the third detector 411 may be less of an issue than the pile-up at the second detector 409. However, as a result of the third photon count being higher than the first photon count, pile-up at the third detector 411 may be more of an issue than the pile-up at the first detector 407. Thus, compared to the second X-ray 408, the first X-ray 406 and the second X-ray 410 measurements at first detector 407 and third detector 411, respectively, will have a bigger pile-up problem.

FIG. 5 shows a pile-up behavior graph 500, which provides an example of pile-up behavior at a PCCT detector of a PCCT system, such as the detectors 407, 408, and 409 of FIG. 4. Pile-up behavior graph 500 shows a relationship between an amount of current applied at an X-ray source of the PCCT system, and an output photon count at the detector. Pile-up behavior graph 500 shows the current in mA along an X axis, and the output photon count along a Y axis, where a dashed line 502 shows an ideal linear relationship between the amount of current applied and the output photon count (where the output photon count matches a number of incoming photons of a beam generated by the current in a 1:1 ratio).

Depending on a number of incoming photons per unit of integration time, a photon-counting detector will have different pile-up behavior. The larger the current and the incoming photon rate, the higher the pile-up behavior. As the pile-up behavior increases, output counts from a piled-up detector will not follow a linear relation with respect to current. Thus, a pile-up correction may be applied to re-establish or approximate linear behavior between current and output counts.

Pile-up behavior graph 500 includes a pile-up curve 504, where the pile-up curve 504 shows an output photon count as the current and number of incoming photons increases. As the number of incoming photons increases (e.g., moving to the right along the X-axis), a divergence between the pile-up curve 504 and the dashed line 502 increases. The greater the divergence between the pile-up curve 504 and a dashed line 502, the more difficult it may be to correct for the pile-up behavior. For example, a first point 506 on the pile-up curve 504 may indicate a first amount of pile-up at the PCCT detector, and a second point 508 on the pile-up curve 504 may indicate a second amount of pile-up at the PCCT detector. A difficulty of correcting for the pile-up may depend on a distance between a point on the pile-up curve 504 and the dashed line 502. For example, the first point 506 may be a first distance 510 along the y axis from the dashed line 502, and the second point 508 may be a second distance 512 along the y axis from the dashed line 502. In other words, as the current increases, a difference between lines 502 and 504 also increases. As a result of the difference increasing between the first point 506 and the second point 508 (e.g., as a result of first distance 510 being longer than the second distance 512), the second point 508 may be more difficult to correct for pile-up than the first point 506.

To correct for pile-up at a detector during a scan, the output counts may be "linearized" to approximate line 502. In one embodiment, each output count and a corresponding current generating the output count may be inputted into a pile-up calibration model, where the pile-up calibration model may output a corrected output photon count that corrects for the pile-up behavior.

The pile-up calibration model may be generated in various ways. In one embodiment, system calibrations are used to create the pile-up calibration model. For example, known materials of different combinations and different thicknesses may be scanned using different current and peak kilovoltage settings. Modeling and calibration vectors may be formed that may be applied to correct count values from a plurality of individual energy bins, such that the corrected count values are linear with respect to an amount of current at a given peak kilovoltage setting. In various embodiments, the generation of the calibration vectors may be based on a combination of physical modeling and real calibration phantom measurements. In other embodiments, the pile-up calibration model may be generated in a different way.

The pile-up correction performed using the pile-up calibration model may be more accurate if the relationship between the currents and the output counts is close to linear. As a result, a pile-up correction may be more accurate at lower current levels (e.g., where the pile-up curve is close to linear) than at higher current levels (e.g., where the pile-up curve is not close to linear). Thus, as described in greater detail below, at high current levels, pile-up may be more accurately corrected by scaling up a corrected output count from a lower current level in accordance with a higher current/lower current ratio than by applying a pile-up correction to the output counts at the higher current.

Figure 6:
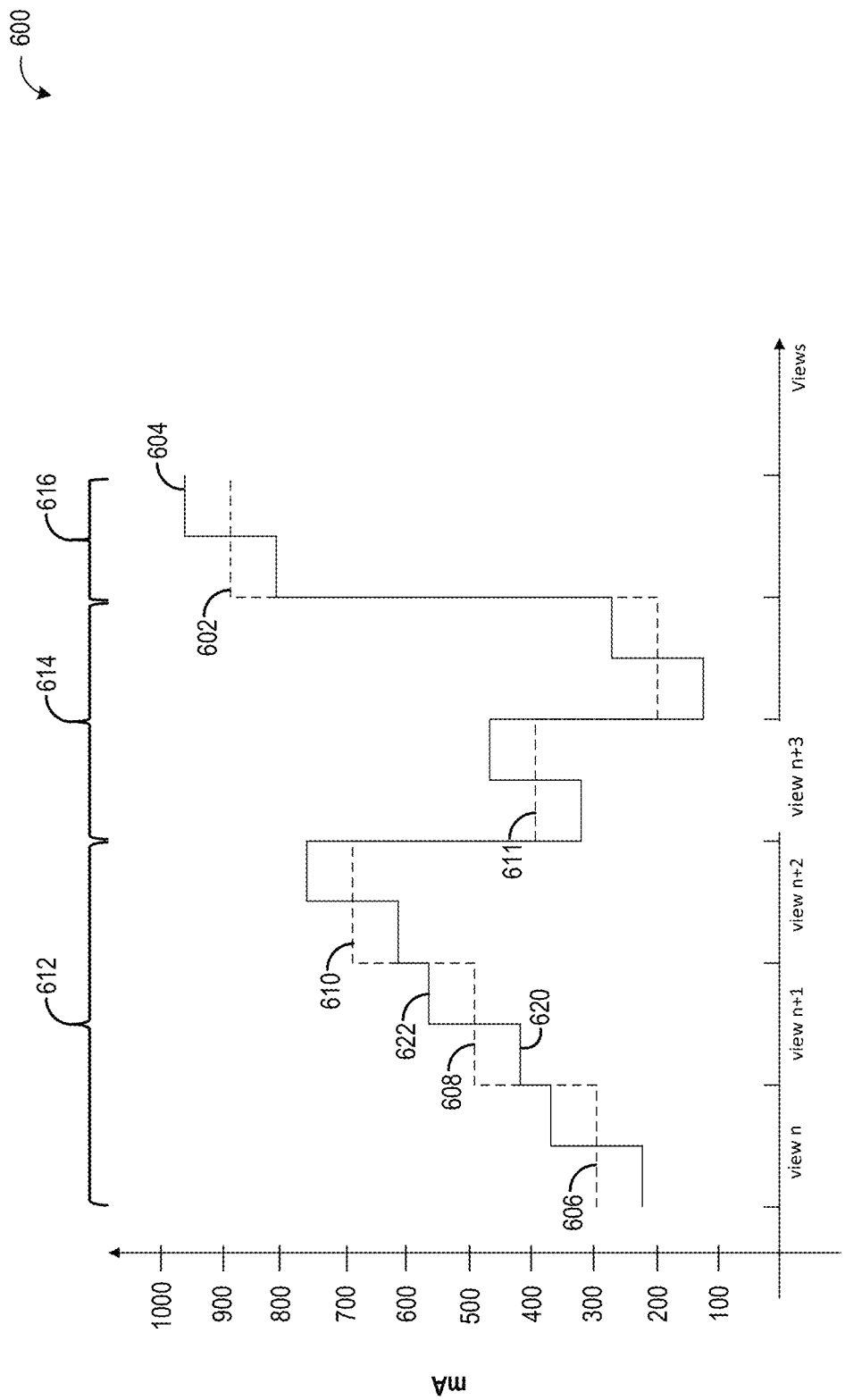
FIG. 6 shows a graph illustrating a modulation curve of a current applied to an X-ray source of a PCCT system in accordance with AEC, in accordance with one or more embodiments of the present disclosure.

Referring now to FIG. 6, an AEC modulation graph 600 is shown, including an example current modulation curve 602 depicted with a dashed line. In a PCCT system, AEC needs to be designed to fulfill image quality and dose requirements. Because pile-up will lower the image quality at a high flux rate, an AEC current modulation should incorporate the pile-up impact and correct for it. For the AEC current modulation, a target current value may be calculated for each view based on a pre-defined function $f$ as shown in equation 1 below. A size and shape of the subject (e.g., a patient) at each view, an IQ target for the AEC, and a characterization of detector pile-up behavior may be inputs to this AEC modulation function:

$$mA(\text{view}) = f(\text{object(view)}, IQ \text{ target}, \text{pileup}) \qquad (1)$$

The function $f$ may be pre-characterized on the PCCT system using different system scan parameters and various subject sizes. Pile-up behavior for each detector pixel is included in the equation to avoid IQ degradation from pile-up when current is increased. A current where the desired IQ target is met for the object being scanned is calculated for each view.

The example current modulation curve 602 shows an amount of current applied in various views n, n+1, n+2, and so on, where the current (e.g., in mA) is represented on the Y axis of AEC modulation graph 600, and the views are indicated on the X axis of AEC modulation graph 600. For example, during a view n, 300 mA current may be applied, as indicated by a dashed portion 606 of the example current modulation curve 602. During view n+1, 500 mA current may be applied, as indicated by a dashed portion 608 of the example current modulation curve 602. During view n+2, 700 mA current may be applied, as indicated by a dashed portion 610 of the example current modulation curve 602, and so on. In other words, a first AEC current modulation design corresponding to example current modulation curve 602 includes increasing a current applied over a first portion 612 of a total number of views; decreasing the current applied over a second portion 614 of the total number of views; increasing the current applied during a third portion 616 of the total number of views; and so on. For example, lower amounts of current may be applied for views where a low amount of attenuation by the object is expected, and higher amounts of current may be applied for views where a high amount of attenuation by the subject is expected. By modulating the current in this manner, a dosage of radiation to which the subject is exposed may be maintained with a desired dosage, while applying more current where needed to image denser portions of the subject with a high image quality, and applying less current for scanning smaller or less dense portions of the subject.

Since current is not constant from view to view, where pile-up is severe (e.g., due to a high current), neighboring views with a lower current may be used to help guide a subsequent pile-up correction performed after scanning the subject. For example, view n+2 has a prescribed current of 700 mA, as indicated by dashed portion 610. A neighboring view n+3 has a prescribed current of 400 mA, as indicated by a dashed portion 611 of the example current modulation curve 602. As a result of the neighboring view n+3 having a lower current, a pile-up correction calculated for view n+3 may be more accurate than a pile-up correction calculated for view n+2, as described above in reference to FIG. 5. To increase an accuracy of the pile-up correction applied at view n+2, the pile-up correction calculated for view n+3 may be used to guide the pile-up correction applied to the output photon count at view n+2.

For example, a pre-established pile-up calibration model may be used to correct the output photon count at a first current at view n+3. If the first current applied at view n+3 is lower than a second current applied at view n+2, rather than using the pile-up calibration model to correct the output photon count at view n+2, the corrected output photon count at view n+3 (generated by the pile-up calibration model) may be scaled up to generate a corrected output photon count at view n+2. In one embodiment, the corrected output photon count for view n+3 may be scaled up based on a ratio of the first current and the second current. For example, if the first current is half of the second current, the corrected output photon count at view n+3 may be scaled up by a factor of two to generate the corrected output photon count at view n+2.

Additionally, the neighboring views may be scanned with different current due to the application of equation (1), which takes into account pile-up as a factor, and as such, the pileup factor used in equation (1) may be selected at least in part to facilitate the current modulation and hence lower current views that can be used to help guide correction of higher current neighboring views. For example, the first current may be modulated based on equation (1) using a first pile-up term, and the second current may be modulated based on equation (1) using a second pile-up term. Thus, by changing the pile-up term in equation (1), a difference in current between the first current and the second current may be selected that maximizes image quality when using this approach.

Additionally, to further increase an accuracy of the pile-up correction, a sub-view current adjustment is proposed. Within each view, a portion of the view may be scanned using a lower current, and another portion of the view may be scanned using a higher current (e.g., a first portion may be scanned using the lower current and a second, remaining portion may be scanned using the higher current). In various embodiments, the first portion may be a first half of the view, and the second portion may be a second half of the view (or vice versa). The lower current and the higher current may be selected such that an average of the lower current and the higher current is equal to the prescribed current for the relevant view, where the prescribed current is indicated by the dashed line of the current modulation curve 602. As a result, for measurements where pile-up impact is severe, two readouts may be achieved from one view at two different current settings. Because the count values achieved at the lower current will have lower pile-up, the pile-up correction applied at the lower current may be used to guide a correction for pile-up at the higher current, as described above. After the correction is applied, the two corrected counts may be added to generate the output count for the view.

A final current modulation curve 604 after correcting for pile-up is indicated with a solid line in AEC modulation graph 600. As can be seen, in each view, rather than applying the amount of current prescribed by example current modulation curve 602, a lesser amount of current is applied during a first half of the view, and a greater amount of current is applied during a second half of the view, where an average of the lesser amount of current and the greater amount of current is equal to the amount of current prescribed by example current modulation curve 602. Because the average is equal to the prescribed amount of current, the dosage of radiation applied to the patient is maintained within the desired level.

For example, in view n+1, rather than applying 500 mA current over the view as prescribed by current modulation curve 602, 425 mA current is applied during a first half 620 of the view n+1, and 575 mA current is applied during a second half 622 of the view n+1, where over the duration of the view, an average of the prescribed 500 mA current is applied. As a result, the dosage of radiation to which the subject is exposed is the same as the dosage implied by current modulation curve 602. However, an amount of pile-up observed during the first half 620 of the view n+1 may be less than an amount of pile-up observed during the second half 622 of the view n+1, and less than an amount of pile-up observed when applying the prescribed 500 mA current as prescribed by the current modulation curve 602, indicated by portion 608.

The lower amount of pile-up may be used to guide a pile-up correction applied to the output photon count of the detector at the view n+1. As described above, the pile-up correction may include using the pre-established pile-up calibration model to correct output photon counts from the lower current of 425 mA, and scaling up the corrected output photon counts to generate corrected output photon counts at the higher current of 500 mA. The corrected output photon counts may be scaled up based on a ratio of the higher current to the lower current. For example, the corrected output photon counts from the lower current of 425 mA may be scaled up 135% to generate the corrected output photon counts at the higher current of 575 mA (e.g., 575/425=1.35). By scaling up the corrected output photon counts at the lower current to generate the corrected output photon counts at the higher current, rather than using the pre-established pile-up calibration model to correct output photon counts from the higher current of 500 mA, an overall accuracy of the pile-up correction may be increased.

Figure 10A:
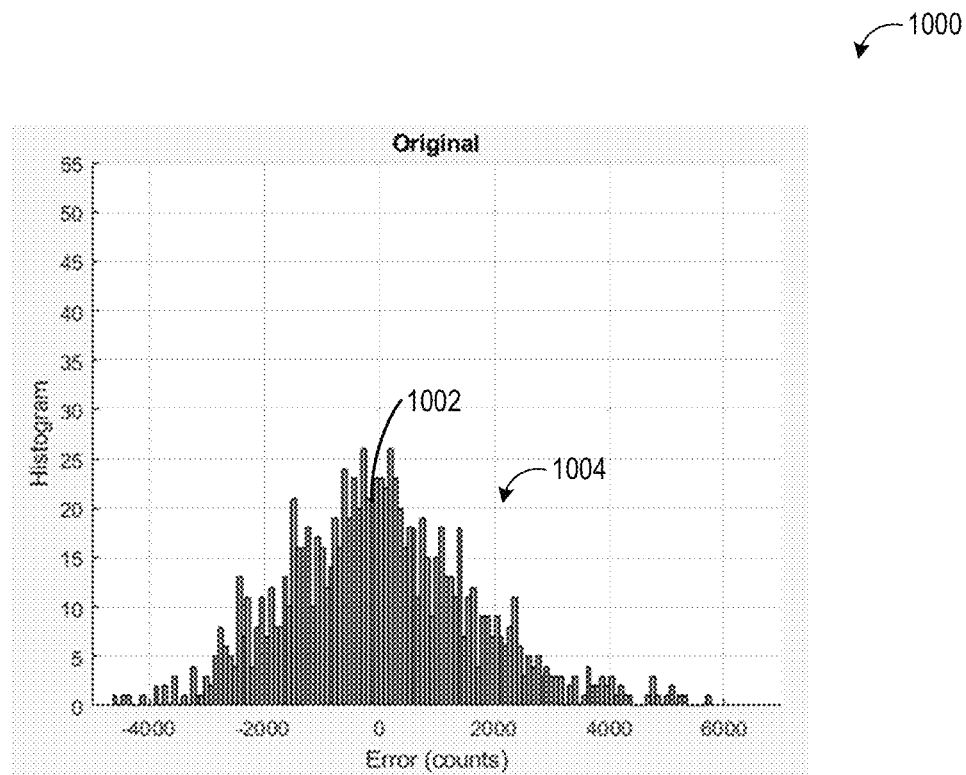
FIG. 10A is a first histogram showing error rates of photon counts based on a traditional approach to pile-up correction.

FIG. 10A shows a first error histogram 1000, which shows error rates in photon counts generated across various views of a scan of a subject in accordance with a traditional approach to pile-up correction. A divergence of an error count from 0 is indicated along an X axis of first error histogram 1000, and a Y axis of first error histogram 1000 indicates a number of views in which a corresponding error count was found. For example, a center bin 1002 of first error histogram 1000 indicates 21 views had an error count of 0, where 0 indicates that an output photon count was the same as an input photon count. A first error distribution 1004 results from the traditional approach to pile-up correction.

Figure 10B:
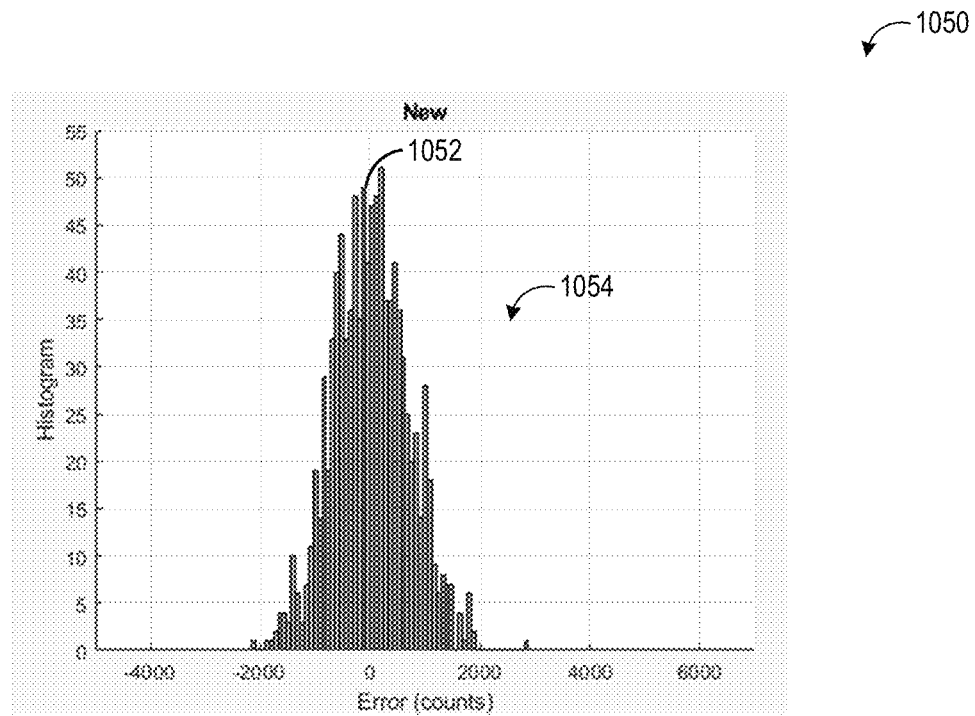
FIG. 10B is a second histogram showing error rates of photon counts based on a proposed approach to pile-up correction; in accordance with one or more embodiments of the present disclosure.

In contrast, FIG. 10B shows a second error histogram 1050, which shows error rates in photon counts generated across various views of a scan of a subject in accordance with the approach to pile-up correction proposed herein. A second error distribution 1054 results from the proposed approach to pile-up correction. As can be seen in FIG. 10B, by using a pile-up correction calculated for a low current readout to guide a pile-up correction for a high current readout, an overall error count is reduced. Additionally, a variance in error across views is reduced.

Figure 7:
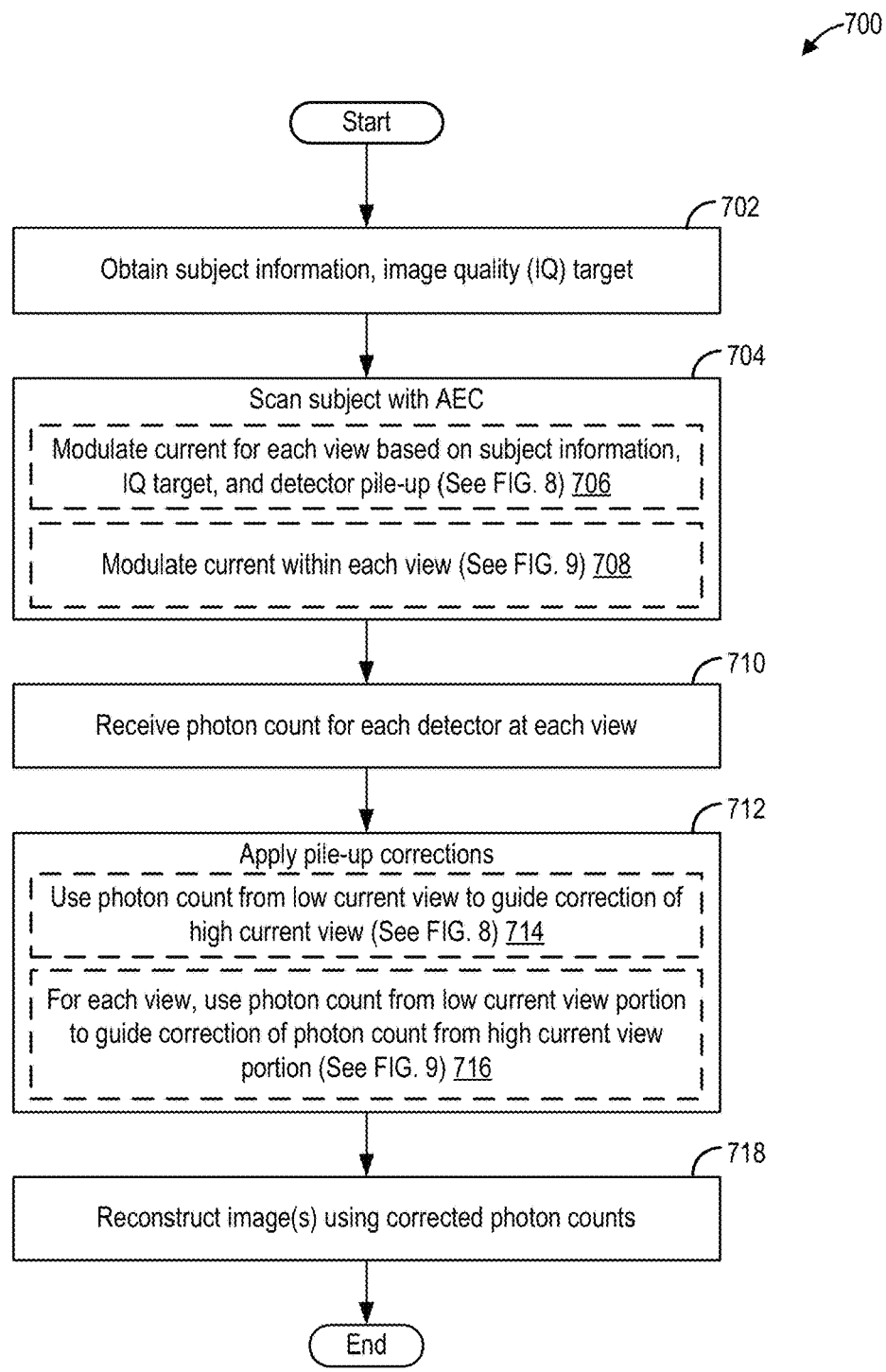
FIG. 7 is a flowchart illustrating an exemplary method for applying a pile-up correction to a readout from photon-counting detectors of a PCCT system in accordance with AEC, in accordance with one or more embodiments of the present disclosure.

Referring now to FIG. 7, an exemplary method 700 is shown for applying a pile-up correction to a readout from a plurality of photon-counting detectors of a PCCT system, such as the PCCT system 100 of FIG. 1. Method 700 and other methods described herein may be executed by a processor of a computing device, based on instructions stored in a memory of the computing device, such as the computing device 216 of the exemplary imaging system 200 of FIG. 2.

Method 700 begins at 702, where method 700 includes obtaining subject information and an image quality (IQ) target. The subject information includes information describing the patient to be scanned which may be input to an AEC optimization model of the PCCT system. To that end, the subject information may include, but is not limited to, patient size, previous exposure history, and so on. In various embodiments, the subject information may be received from an operator of the PCCT system.

In some examples, method 700 may automatically determine the patient size, for example, by performing a scout scan of the patient, and calculating the patient size based on projection data acquired during the scout scan. For example, patient size may be expressed in terms of a water-equivalent diameter Dw, which may be calculated based on CT numbers of projection data from the scout scan. Since the region of a patient being scanned may not be uniform in size, the water-equivalent diameter Dw may be calculated for each projection angle. In this way, the dose level may be adapted throughout the region being scanned based on the patient size at each angle. Alternatively, in some examples a single water-equivalent diameter Dw may be used to describe the patient size.

In some examples, the water-equivalent diameter D, may be estimated without the use of a scout scan. For example, D, can be estimated by a user with personal experience or from references of suitable body size parameters (e.g., body height and/or weight). It should also be appreciated that in some examples, the patient size may be expressed in terms other than the water-equivalent diameter.

Previous exposure history of the patient may be taken into account when determining radiation dose level. For example, the previous exposure history may provide constraints (e.g., an upper limit) on the dose level, such that patients with large amounts of previous radiation exposure may be presently exposed to lower dose levels than patients with small amounts of previous radiation exposure. Previous exposure history can also be used as a reference to guide the appropriate dose target selection for the patient under study.

In various embodiments, the IQ target may be selected by the operator. The IQ target may describe a target noise level, such as an image pixel standard deviation. In other embodiments, the IQ target may be based on a plurality of factors impacting image quality. Further, the image quality may be empirically characterized as a function of dose index. For example, a phantom-based study may be performed to measure image quality for a plurality of peak X-ray tube kilovoltages at a given water-equivalent diameter. Such a study may further be based on a clinical task. In various embodiments, the IQ target may be obtained from a scan protocol.

At 704, method 700 includes scanning the subject with AEC. With AEC, a current modulation scheme may be designed using an optimization model. The optimization model may determine an optimized dose level and an optimized scan protocol based on the IQ target, the subject information, and/or other received inputs and/or selections. For example, the optimized dose level may be determined based on information stored in a lookup table in a memory of the PCCT system, where the optimized dose level is determined based on the IQ target selection, the patient size, and a clinical task. The optimized scan protocol may then be generated based on the optimized dose level. The optimized scan protocol may indicate how a current applied by the PCCT system may be modulated for each view, for example, to provide a consistent contrast to noise ratio (CNR) at a plurality of detectors of a detector array of the PCCT system.

At 706, scanning the subject with AEC includes modulating a current for each view based on the subject information, IQ target, and detector pile-up. Modulating the current across views based on the subject information, IQ target, and detector pile-up is described in greater detail below in reference to FIG. 8.

At 708, method 700 includes modulating the current within each view in accordance with an intra-view current modulation. The intra-view current modulation may maintain an amount of radiation applied to the subject within a dosage prescribed by the optimized scan protocol, while generating a more accurate pile-up correction to a photon count outputted by a detector. Modulating the current within each view is described in greater detail in reference to FIG. 9.

At 710, method 700 includes receiving a photon count for each detector at each view.

At 712, method 700 includes applying pile-up corrections at each detector at each view. At 714, applying the pile-up corrections includes using a photon count from a low current view to guide correction of a high current view. As described above in reference to FIGS. 5 and 6, a pile-up correction calculated for a low current view may be advantageously used to generate a more accurate pile-up correction for a neighboring high current view. Generating a high current pile-up correction from a neighboring low current pile-up correction is described in greater detail below in reference to FIG. 8.

At 716, applying the pile-up corrections includes, for each view and within each view, using a photon count from a low current view portion to guide correction of a photon count from a high current view portion. Using the photon count from the low current view portion to guide correction of a photon count from the high current view portion is described in greater detail below in reference to FIG. 9. In various embodiments, the pile-up correction may be calculated based on measurements taken collectively from all energy bins, and then applied to each energy bin individually. After the correction is performed, the output counts from each bin are expected to be linear with respect to the current applied.

At 718, method 700 includes reconstructing one or more images using the corrected photon counts, and method 700 ends.

Figure 8:
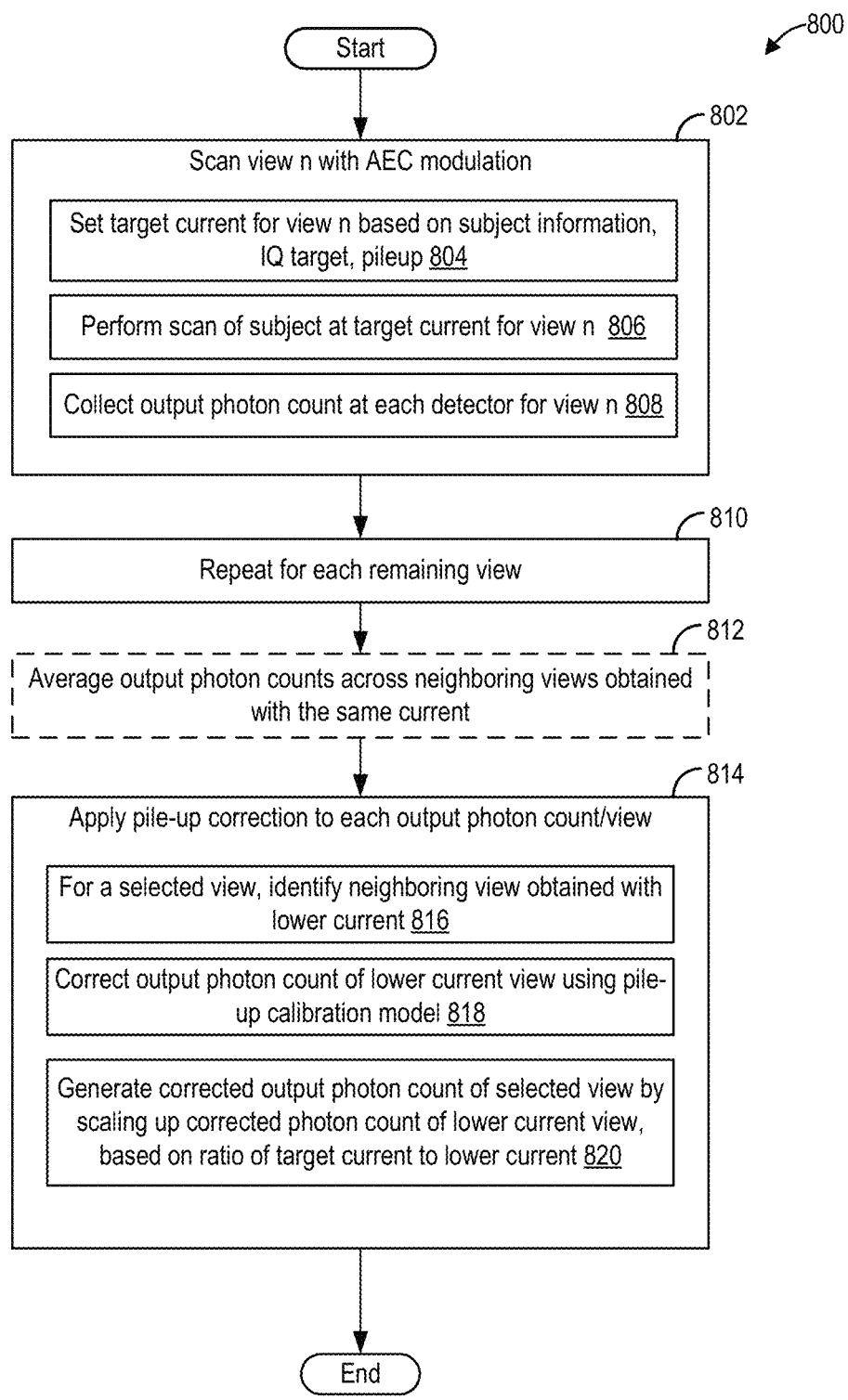
FIG. 8 is a flowchart illustrating an exemplary method for correcting for pile-up behavior using current modulation between views acquired by a PCCT system, in accordance with one or more embodiments of the present disclosure.

Referring now to FIG. 8, a first exemplary method 800 is shown for correcting for pile-up behavior within a PCCT system, such as the PCCT system 100 of FIG. 1. In method 800, for a given view, pile-up behavior at each detector of a detector array of the PCCT system may be corrected by applying a pile-up correction, where the pile-up correction is generated based on a photon count from the detector at a neighboring view with a lower current.

Method 800 begins at 802, where method 800 includes scanning a view n of the subject in accordance with an AEC current modulation. Scanning the view n includes, at 804, setting a target current for the view based on the subject information, IQ target, and a pile-up factor. The pile-up factor can be a quantitative measure of the severity of pile-up with respect to the X-ray tube current being used. At 806, scanning the view n includes performing the scan of the subject for the view n at the target current. At 808, scanning the view n includes collecting an output photon count at each detector for the view n.

At 810, method 800 includes repeating steps 804, 806, and 808 for each remaining view. For each remaining view, the subject is scanned at a different target current prescribed by the AEC current modulation (e.g., based on the subject information, IQ target, and pile-up factor). As described in reference to the exemplary AEC modulation graph of FIG. 6, the target current may be adjusted from a first target current to a second, different target current due to a change in a predicted attenuation of X-ray beams through the subject, where the X-ray beams are generated by the target current. For example, for a first view, the first target current may be low, due to a low predicted attenuation of the X-ray beams (e.g., for photons passing through soft tissues of the subject, or around the subject). For a second view, the second target current may be higher, due to a higher predicted attenuation of the X-ray beams (e.g., for photons passing through bone of the subject). Thus, some views of a plurality of views of the scan may have neighboring views that are scanned with a lower target current.

At 812, method 800 may include averaging output photon counts at one or more detectors across neighboring views obtained with a same or substantially similar current (e.g., where target currents of the neighboring views are within a threshold current difference). For example, a given detector may output a first photon count in a first view; a second photon count in a second, neighboring view; and a third photon count in a third, neighboring view. If a target current applied during the first view, the second, neighboring view, and the third, neighboring view is the same or substantially similar, an average of the first photon count, the second photon count, and the third photon count may be calculated. The first photon count of the detector during the first view may then be replaced with the average photon count; the second photon count of the detector during the second, neighboring view may be replaced with the average photon count; and the third photon count of the detector during the third, neighboring view may be replaced with the average photon count. By averaging the output photon counts across neighboring views obtained with the same current, an amount of noise in the output photon counts may be reduced.

At 814, method 800 includes applying a pile-up correction to each output photon count per view, for a plurality of views of the scan. For example, after photon counts have been collected at each detector for each view of the scan, a program running on a computing device of the PCCT system may iterate through all of the views of the scan, and apply a pile-up correction to each photon count outputted by each detector during the relevant view.

At 816, applying the pile-up correction to each output photon count per view at each detector includes, for a selected view, identifying a neighboring view obtained with a lower current than the selected view. The neighboring view may be a consecutive view of the selected view, or the neighboring view may be a view within a threshold number of consecutive views of the selected view. For example, the selected view may be scanned at a target current of 400 mA, and the threshold number of views may be 5. In a first example, a consecutive view of the selected view may be scanned at a target current of 300 mA, where the consecutive view may be identified as a neighboring view with a lower current than the selected view. In a second example, a first consecutive view of the selected view may be scanned at a target current of 400 mA, where the first consecutive view may not be identified as a neighboring view with a lower current than the selected view. A second consecutive view of the selected view may also be scanned at a target current of 400 mA, where the second consecutive view may not be identified as a neighboring view with a lower current than the selected view. A third consecutive view of the selected view may be scanned at a target current of 300 mA, where the third consecutive view may be identified as a neighboring view with a lower current than the selected view, as the third consecutive view is within the threshold number of 5 views.

At 818, applying the pile-up correction to each output photon count per view includes correcting the output photon count of the lower current view. The output photon count of the lower current view may be corrected using a pile-up calibration model that takes the output photon count and the lower current as input, and outputs a corrected output photon count.

At 820, applying the pile-up correction to each output photon count per view includes correcting the output photon count for the selected view based on the corrected output photon count for the lower current view. In various embodiments, the corrected output photon count for the lower current view may be multiplied by a factor (e.g., a proportional factor) to generate the corrected output photon count for the selected view. The proportional factor may be based on a ratio of the target current to the lower current. For example, if the lower current is ¼ of the target current, the proportional factor may be 4, whereby the corrected output photon count for the lower current view may be multiplied by 4 to generate the corrected output photon count for the selected view.

In other words, for the neighboring views, an assumption can be made that the same object path lengths are being scanned, because the neighboring views are very close to each other. For the same object, the target (e.g., higher) current will be associated with higher pileup than the lower current. To increase the accuracy of the pile-up correction for the target current, rather than using the pile-up calibration model, corrected photon counts at the lower current view may be scaled up (e.g., multiplied by a ratio of the target current to the lower current) to account for pile-up at the higher, target current view.

In some embodiments, applying the pile-up correction to each output photon count per view by correcting the output photon count for the selected view based on the corrected output photon count for the lower current view may include generating a corrected output photon count for the selected view using the pile-up calibration model (which may also be referred to as an initial corrected photon count), and then adjusting the (initial) corrected output photon count outputted by the pile-up calibration model based on the scaled-up, corrected photon counts at the lower current view. For example, the output photon count of the higher current view may also be corrected using the pile-up calibration model, where the output photon count at the higher current may be inputted into the model, to receive as output the corrected output photon count at the higher current view. The corrected output photon count at the higher current view may then be compared with the scaled-up corrected output photon count from the lower current view. If a difference between the corrected output photon count at the higher current view and the scaled-up corrected output photon count from the lower current view exceeds a threshold, the scaled-up corrected output photon count from the lower current view may be used to adjust the corrected output photon count at the higher current view. Alternatively, the corrected output photon count at the higher current view may be used to adjust the scaled-up corrected output photon count from the lower current view.

For some photon counts at some detectors, no neighboring views with a lower current may be identified. In such cases, a pile-up correction may be applied to the relevant photon count based on a current applied at the relevant view. Alternatively, a sliding window approach may be used, where currents at a fixed number of neighboring views are compared to determine a view with a lowest current, and the pile-up curve is obtained for the view with the lowest current. The pile-up curve obtained for the view with the lowest current may then be used to correct the photon count at the detector for the view with the lowest current, as well as the view with the higher current.

While FIG. 8 was described above as the photon counts being corrected after some or all views have been obtained, it should be appreciated that the photon counts may be corrected immediately after each view is obtained or after a certain number of views have been obtained. In such examples, the observed pileup may be used to guide the selection of the current used to obtain subsequent views. For example, if a relatively high pileup is observed for a given view, the current used to obtain the next view may be adjusted (e.g., lowered) so that the next view may be used to guide the correction of the pileup of the subsequent view. In doing so, the observed pileup may be used to modulate the current in real-time.

Figure 9:
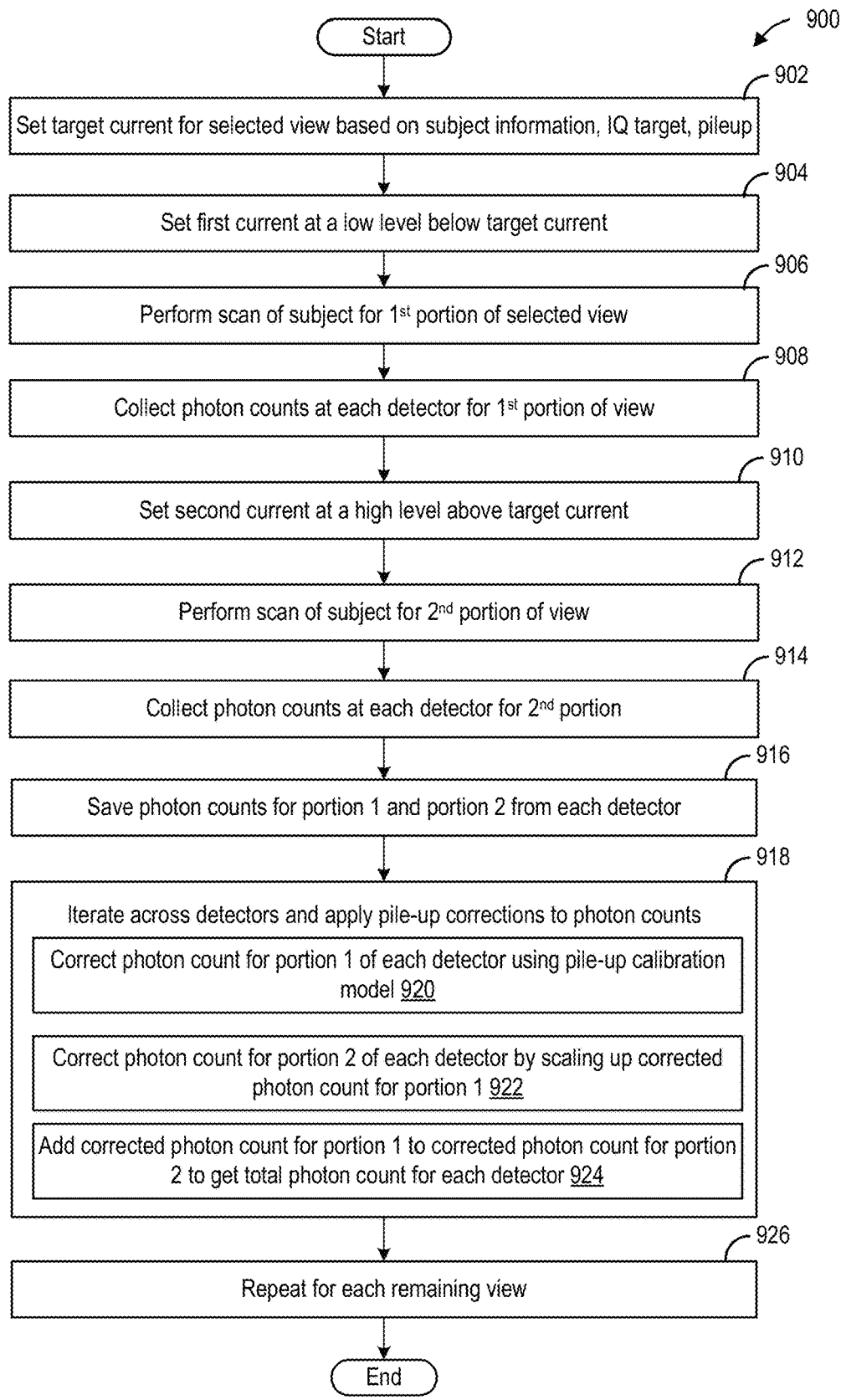
FIG. 9 is a flowchart illustrating an exemplary method for correcting for pile-up behavior using current modulation within a view acquired by a PCCT system, in accordance with one or more embodiments of the present disclosure.

Turning now to FIG. 9, a second exemplary method 900 is shown for correcting for pile-up behavior within a PCCT system, such as the PCCT system 100 of FIG. 1. In method 900, for a given view, pile-up behavior at each detector of a detector array of the PCCT system may be corrected by applying a pile-up correction, where the pile-up correction is generated based on a photon count from the detector at a portion of the view with a lower current.

Method 900 begins at 902, where method 900 includes setting a target current for a selected view based on subject information, an IQ target, and the pile-up factor, as described above in reference to FIG. 8.

At 904, method 900 includes setting a first current applied to an X-ray source of the PCCT system, where the first current is at a level lower than the target current. The lower mA value can be picked based on the hardware capability using a predefined percentage setting with respect to the target current.

At 906, method 900 includes performing a scan of the subject for a first portion of the selected view. In various embodiments, the first portion of the selected view may be half of the selected view. At 908, method 900 includes collecting photon counts at each detector for the first portion of the selected view.

At 910, method 900 includes setting a second current applied to the X-ray source, where the second current is at a higher level than the target current. In various embodiments, the first current and the second current may be selected such that an average of the first current and the second current is the target current.

At 912, method 900 includes performing a scan of the subject for a second portion of the selected view. The second portion of the selected view may be half of the selected view, whereby performing the scan of the subject for the second portion of the selected view may complete the scan of the subject. At 914, method 900 includes collecting photon counts at each detector for the second portion of the selected view.

For example, the first current may be applied to the X-ray source for a first duration, and the second current may be applied to the X-ray source for a second duration, where the first duration is equal to the second duration. As a result of applying the first current for the first duration and the second current for the second duration, the scan of the selected view may be divided into two equal portions, the first portion and the second portion. For each of the first portion of a second portion, photon counts outputted by each detector are collected, such that a total photon count for each detector for the selected view may be a sum of a first photon count collected during the first portion of the selected view, and a second photon count collected during the second portion of the selected view. In other embodiments, the first duration may not be the same as the second duration. For example, the first duration and the second duration may be selected in accordance with the following equation:

(first duration time*first current)+(second duration time*second current)=(1)target current*(first duration time+second duration time)

At 916, method 900 includes saving the first photon count and the second photon count from each detector for the selected view. For example, the first photon count and the second photon count from each detector may be stored in a vector of photon count pairs for the selected view.

When all of the photon count pairs for the selected view have been collected, at 918, method 900 includes iterating across the detectors and applying pile-up corrections to the saved photon counts at each detector.

At 920, applying the pile-up corrections to the saved photon counts at each detector includes correcting the photon count of the first portion of the selected view. The photon count of the first portion of the selected view may be corrected using a pile-up calibration model that takes the photon count and the low current as input, and outputs a corrected photon count.

At 922, applying the pile-up corrections to the saved photon counts at each detector includes correcting the photon count for the second portion of the selected view based on the corrected photon count from the first portion of the selected view. In various embodiments, the corrected photon count for the first portion of the selected view may be multiplied by a factor to generate the corrected photon count for the second portion of the selected view. The factor may be based on a ratio of the target current applied during the second portion and the lower current applied during the first portion, as described above in reference to FIG. 8. Additionally, in some embodiments, applying the pile-up corrections to the saved photon counts at each detector may include generating a corrected output photon count for the second portion of the selected view using the pile-up calibration model, and then adjusting the corrected output photon count outputted by the pile-up calibration model based on the scaled-up, corrected photon counts from the first portion of the selected view. For example, the output photon count of the second portion of the selected view may also be corrected using the pile-up calibration model, where the output photon count at the second current and the second current may be inputted into the model, to receive as output the corrected output photon count at the second portion of the selected view. The corrected output photon count at the second portion of the selected view may then be compared with the scaled-up corrected output photon count from the first portion of the selected view. The scaled-up corrected output photon count from the first portion of the selected view may be used to adjust the corrected output photon count at the second portion of the selected view. Alternatively, the corrected output photon count at the second portion of the selected view may be used to adjust the scaled-up corrected output photon count from the first portion of the selected view.

At 924, applying the pile-up corrections to the saved photon counts at each detector includes adding the corrected first photon count to the corrected second photon count (after scaling) to get a total corrected photon count for the detector. The corrected total photon count for the detector may be used to reconstruct an image, where a quality of the image may be higher than an image reconstructed from an uncorrected total photon count. At 926, method 900 includes repeating steps 902-924 for each remaining view, and method 900 ends.

While FIG. 9 was described above as the photon counts being corrected after some or all views have been obtained, it should be appreciated that the photon counts may be corrected immediately after each view is obtained or after a certain number of views have been obtained. In such examples, the observed pileup may be used to guide the selection of the current used to obtain subsequent views. For example, if a relatively high pileup is observed for a given view, the current used to obtain the next view may be adjusted (e.g., lowered) so that the next view may be used to guide the correction of the pileup of the subsequent view. In doing so, the observed pileup may be used to modulate the current in real-time.

Thus, two methods are described for correcting a first photon count output by a detector during a first view or a first portion of a first view to generate a corrected first photon count, and correcting a second photon count output by the detector during a second view or a second portion of the first view based on the correction to the first photon count to generate a corrected second photon count. The corrections to the photon counts described herein may use a pile-up correction calculated for a detector at a lower current to guide a pile-up correction at the detector for a higher current. In both methods, the current may be modulated between views in accordance with an AEC modulation scheme. In a first method (e.g., method 800), a first pile-up correction calculated for a low photon count at a first view is used to guide a second pile-up correction applied to a high photon count at a second view. In the second method (e.g., method 900, the current is additionally modulated within each view, where a first pile-up correction calculated for a first, lower photon count collected at a first portion of the view scanned at a lower current is used to guide a second pile-up correction applied to second, higher photon count collected at a second portion of the view scanned at a higher current. The first pile-up correction may be generated by a pile-up calibration model, based on the lower photon count and the lower current. The first pile-up correction may be used to guide the second pile-up correction by multiplying corrected photon counts from the first pile up correction by a proportional factor, such as a ratio between the higher current and the lower current, to generate scaled photon counts. These scaled photon counts can be used to correct the photon counts for the high current views/view portions, by either replacing the photon counts for the high current views/view portions or by adjusting initial corrected photon counts (corrected by the calibration model). By using the first pile-up correction to guide the second pile-up correction, as opposed to relying on the pile-up calibration model to generate corrected photon counts at the higher current, an overall quality of an image reconstructed using the corrected photon counts may be improved. The technical effect of using the first pile-up correction to guide the second pile-up correction, as opposed to relying on the pile-up calibration model to generate corrected photon counts at the higher current, is that pile-up behavior at higher current levels may be more accurately corrected, resulting in higher quality image reconstructions.

In another representation, a method for a photon-counting computed tomography (PCCT) system includes correcting a first photon count output by a detector of the PCCT system during a first portion of a view to generate a corrected first photon count, and correcting a second photon count output by the detector during a second portion of the view based on the correction to the first photon count to generate a corrected second photon count, and reconstructing an image from the corrected first photon count and the corrected second photon count. In a first example of the method, correcting the second photon count based on the correction to the first photon count comprises scaling the corrected first photon count based on a ratio of a first current of the PCCT system during the first view portion to a second current of the PCCT system during the second view portion to generate a scaled corrected first photon count and correcting the second photon count based on the scaled corrected first photon count. In a second example of the method, optionally including the first example, correcting the second photon count based on the scaled corrected first photon count includes setting the corrected second photon count to be the scaled corrected first photon count. In a third example of the method, optionally including one or both of the first and second examples, correcting the second photon count based on the scaled corrected first photon count includes entering the second photon count as input to a calibration model to generate an initial corrected second photon count, and adjusting the initial corrected second photon count based on the scaled corrected first photon count to generate the corrected second photon count. In any of the above examples, the first current of the PCCT system during the first view portion is lower than the second current of the PCCT system during the second view portion.

The disclosure also provides support for a method for a photon-counting computed tomography (PCCT) system, the method comprising: during a scan of a subject, adjusting an X-ray tube output current of the PCCT system across and/or within one or more views, the current adjusted between a first current and a second current, the first current higher than the second current, for a view of the one or more views scanned by the PCCT system, applying a first pile-up correction to a first photon count output at a detector of a detector array of the PCCT system at the first current, the first pile-up correction based on a second pile up correction applied to a second photon count output at the detector at the second current, and reconstructing an image based on the corrected first photon count and the corrected second photon count, and outputting the image to a display device of the PCCT system. In a first example of the method, adjusting the X-ray tube output current of the PCCT system within and/or across the one or more views further comprises adjusting the X-ray tube output current of the PCCT system from the first current for a first view to the second current for a second view, where the first current is selected based on a size and/or shape of the subject at the first view, a target image quality, and a first pileup term at the first view, and the second current is selected based on a size and/or shape of the subject at the second view, the target image quality, and a second pile-up term at the second view, the second pile-up term different from the first pile-up term. In a second example of the method, optionally including the first example, the second pileup correction applied to the second photon count is based on an output of a pile-up calibration model, the pile-up calibration model taking as input the second photon count and the second current to generate the corrected second photon count. In a third example of the method, optionally including one or both of the first and second examples, the method further includes multiplying the corrected second photon count by a ratio of the first current to the second current to generate a scaled second photon count, and wherein applying the first pile-up correction to the first photon count output includes inputting the first photon count and the first current into the pile-up calibration model to generate an initial corrected first photon count, and adjusting the initial corrected first photon count based on the scaled second photon count to generate the corrected first photon count. a corrected second photon count outputted by the pile-up calibration model is multiplied by a ratio of the first current to the second current to generate a scaled second photon count, and applying the first pile-up correction to the first photon count output includes inputting the first photon count and the first current into the pile-up calibration model to generate a corrected first photon count, and one of: adjusting the corrected first photon count based on the scaled second photon count, and replacing the corrected first photon count with the scaled first second photon count. In a fourth example of the method, optionally including one or more or each of the first through third examples, the method further includes multiplying the corrected second photon count by a ratio of the first current to the second current to generate a scaled second photon count, and wherein applying the first pile-up correction to the first photon count includes replacing the first photon count with the scaled second photon count to generate the corrected first photon count. In a fifth example of the method, optionally including one or more or each of the first through fourth examples, the X-ray tube output current is adjusted to the first current to scan a first view, and the X-ray tube output current is adjusted to the second current to scan a second view, the second view different from the first view. In a sixth example of the method, optionally including one or more or each of the first through fifth examples, the second view is within a threshold number of subsequent consecutive views of the first view. In a seventh example of the method, optionally including one or more or each of the first through sixth examples, the X-ray tube output current is adjusted to the first current for a first portion of a view, and the X-ray tube output current is adjusted to the second current for a second portion of the view. In an eighth example of the method, optionally including one or more or each of the first through seventh examples, the first current is higher than a target current prescribed for the view by an AEC current modulation design scheme, and the second current is lower than the target current, and an average of the first current and the second current is the target current. In a ninth example of the method, optionally including one or more or each of the first through eighth examples, the first photon count is a first number of photons detected at the detector during the first portion of the view, and the second photon count is a second number of photons detected at the detector during the second portion of the view, and a total photon count at each detector for the view is a sum of the corrected first photon count and a corrected second photon count, the corrected second photon count a result of applying the pile-up correction to the second photon count. In a tenth example of the method, optionally including one or more or each of the first through ninth examples, applying the pile-up correction to the first photon count output at each detector of the detector array includes applying the pile-up correction across all energy bins of each detector.

The disclosure also provides support for a method for a photon-counting computed tomography (PCCT) system, the method comprising: during scanning of a view of a subject using the PCCT system: applying a first current to an x-ray source of the PCCT system for a first portion of the view, applying a second current to the x-ray source for a second portion of the view, for each detector of the PCCT system: applying a first pile-up correction to a first photon count output by the detector during the first portion of the view to generate a corrected first photon count, and applying a second pile-up correction to a second photon count output by the detector during the second portion of the view to generate a corrected second photon count, the first pile-up correction applied to the first photon count based on the second pile-up correction applied to the second photon count, summing the corrected first photon count and the corrected second photon count to generate a total output photon count for the detector, and reconstructing an image based on the total output photon count at each detector. In a first example of the method, the first current is higher than a target current prescribed for the view by an Automatic Exposure Control (AEC) modulation of the PCCT system, the second current is lower than the target current, and the target current is an average of the first current and the second current. In a second example of the method, optionally including the first example, applying the second pile-up correction to the second photon count to generate the corrected second photon count further comprises inputting the second photon count and the second current into a pre-established pile-up calibration model, and receiving the corrected second photon count as an output of the pre-established pile-up calibration model. In a third example of the method, optionally including one or both of the first and second examples, applying the first pile-up correction to the first photon count based on the second pile-up correction comprises generating the corrected first photon count by scaling the corrected second photon count up by a factor. In a fourth example of the method, optionally including one or more or each of the first through third examples, the factor is based on a ratio of the first current to the second current. In a fifth example of the method, optionally including one or more or each of the first through fourth examples, the corrected first photon count is further generated based on an initial corrected first photon count, the initial corrected first photon count output by the pre-established pile-up calibration model based on the first photon count and the first current.

The disclosure also provides support for a photon-counting computed tomography (PCCT) system, comprising: an x-ray source that emits a beam of x-rays toward a subject to be imaged, a photon-counting detector that receives the beam of x-rays attenuated by the subject, a data acquisition system (DAS) operably connected to the detector, and a computer comprising non-transitory memory and operably connected to the DAS, wherein the computer is configured with instructions in the non-transitory memory that when executed cause the computer to: for each view n scanned by the PCCT system: adjust an automatic Exposure Control (AEC) current modulation to alternately increase an X-ray tube output current of the PCCT system above a prescribed current and decrease the X-ray tube output current below the prescribed current, the AEC current modulation determined by an AEC modulation function including a correction for pile-up, collect a first photon count at each detector of the PCCT system at the increased X-ray tube output current, collect a second photon count at each detector at the decreased X-ray tube output current, apply a first pile-up correction to the second photon count at each detector to obtain a corrected second photon count, the first pile-up correction based on the second photon count, apply a second pile-up correction to the first photon count at each detector to obtain a corrected first photon count, the second pile-up correction based on the first pile-up correction and the corrected second photon count, add the first corrected photon count to the second corrected photon count at each detector to obtain a total output photon count at each detector, and reconstruct an image based on the total output photon count at each detector, and output the image to a display device of the PCCT system. In a first example of the system, alternately increasing the X-ray tube output current of the PCCT system above the prescribed current and decreasing the X-ray tube output current below the prescribed current further comprises increasing the X-ray tube output current to a first high current for a first duration, and decreasing the X-ray tube output current to a second low current for a second duration, the prescribed current equal to an average of the first high current and the second low current. In a second example of the system, optionally including the first example, the first pile-up correction is an output of a pile-up calibration model that takes as inputs the second photon count and the decreased X-ray tube output current. In a third example of the system, optionally including one or both of the first and second examples, applying the second pile-up correction to the first photon count at each detector, the second pile-up correction based on the first pile-up correction further comprises: multiplying the corrected second photon count by a proportional factor, the proportional factor is based on a ratio of the increased X-ray tube output current to the decreased X-ray tube output current.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method for a photon-counting computed tomography (PCCT) system, the method comprising:
during a scan, adjusting an X-ray tube output current of the PCCT system across and/or within one or more views, the current adjusted between a first current and a second current, the first current higher than the second current;
for a view of the one or more views scanned by the PCCT system, applying a first pile-up correction to a first photon count output at a detector of a detector array of the PCCT system at the first current, the first pile-up correction based on a second pile up correction applied to a second photon count output at the detector at the second current; and
reconstructing an image based on the corrected first photon count and the corrected second photon count, and outputting the image to a display device of the PCCT system.

2. The method of claim 1, wherein adjusting the X-ray tube output current of the PCCT system within and/or across the one or more views further comprises adjusting the X-ray tube output current of the PCCT system from the first current for a first view to the second current for a second view, where the first current is selected based on a size and/or shape of a subject at the first view, a target image quality, and a first pileup term at the first view, and the second current is selected based on a size and/or shape of the subject at the second view, the target image quality, and a second pile-up term at the second view, the second pile-up term different from the first pile-up term.

3. The method of claim 1, wherein the second pileup correction applied to the second photon count is based on an output of a pile-up calibration model, the pile-up calibration model taking as input the second photon count and the second current to generate the corrected second photon count.

4. The method of claim 3, further comprising multiplying the corrected second photon count by a ratio of the first current to the second current to generate a scaled second photon count, and wherein applying the first pile-up correction to the first photon count output includes inputting the first photon count and the first current into the pile-up calibration model to generate an initial corrected first photon count, and adjusting the initial corrected first photon count based on the scaled second photon count to generate the corrected first photon count.

5. The method of claim 3, further comprising multiplying the corrected second photon count by a ratio of the first current to the second current to generate a scaled second photon count, and wherein applying the first pile-up correction to the first photon count includes replacing the first photon count with the scaled second photon count to generate the corrected first photon count.

6. The method of claim 1, wherein the X-ray tube output current is adjusted to the first current to scan a first view, and the X-ray tube output current is adjusted to the second current to scan a second view, the second view different from the first view.

7. The method of claim 6, wherein the second view is within a threshold number of subsequent consecutive views of the first view.

8. The method of claim 1, wherein the X-ray tube output current is adjusted to the first current for a first portion of a view, and the X-ray tube output current is adjusted to the second current for a second portion of the view.

9. The method of claim 8, wherein the first current is higher than a target current prescribed for the view by an AEC current modulation design scheme, and the second current is lower than the target current, and an average of the first current and the second current is the target current.

10. The method of claim 8, wherein the first photon count is a first number of photons detected at the detector during the first portion of the view, and the second photon count is a second number of photons detected at the detector during the second portion of the view, and a total photon count at each detector for the view is a sum of the corrected first photon count and a corrected second photon count.

11. The method of claim 1, wherein applying the pile-up correction to the first photon count output at each detector of the detector array includes applying the pile-up correction across all energy bins of each detector.

12. A method for a photon-counting computed tomography (PCCT) system, the method comprising:
during scanning using the PCCT system:
applying a first current to an X-ray source of the PCCT system for a first portion of the view;
applying a second current to the X-ray source for a second portion of the view;
for each detector of the PCCT system:
applying a first pile-up correction to a first photon count output by the detector during the first portion of the view to generate a corrected first photon count, and applying a second pile-up correction to a second photon count output by the detector during the second portion of the view to generate a corrected second photon count, the first pile-up correction applied to the first photon count based on the second pile-up correction applied to the second photon count;
summing the corrected first photon count and the corrected second photon count to generate a total output photon count for the detector; and
reconstructing an image based on the total output photon count at each detector.

13. The method of claim 12, wherein the first current is higher than a target current prescribed for the view by an Automatic Exposure Control (AEC) modulation of the PCCT system, the second current is lower than the target current, and the target current is an average of the first current and the second current.

14. The method of claim 12, wherein applying the second pile-up correction to the second photon count to generate the corrected second photon count further comprises inputting the second photon count and the second current into a pre-established pile-up calibration model, and receiving the corrected second photon count as an output of the pre-established pile-up calibration model.

15. The method of claim 14, wherein applying the first pile-up correction to the first photon count based on the second pile-up correction comprises generating the corrected first photon count by scaling the corrected second photon count up by a factor based on a ratio of the first current to the second current.

16. The method of claim 15, wherein the corrected first photon count is further generated based on an initial corrected first photon count, the initial corrected first photon count output by the pre-established pile-up calibration model based on the first photon count and the first current.

17. A photon-counting computed tomography (PCCT) system, comprising:
an X-ray source that emits a beam of X-rays toward a subject to be imaged;
a photon-counting detector that receives the beam of X-rays attenuated by the subject;
a data acquisition system (DAS) operably connected to the detector; and
a computer comprising non-transitory memory and operably connected to the DAS, wherein the computer is configured with instructions in the non-transitory memory that when executed cause the computer to:
for each view n scanned by the PCCT system:
adjust an Automatic Exposure Control (AEC) current modulation to alternately increase an X-ray tube output current of the PCCT system above a prescribed current and decrease the X-ray tube output current below the prescribed current, the AEC current modulation determined by an AEC modulation function including a correction for pile-up;
collect a first photon count at each detector of the PCCT system at the increased X-ray tube output current;
collect a second photon count at each detector at the decreased X-ray tube output current;
apply a first pile-up correction to the second photon count at each detector to obtain a corrected second photon count, the first pile-up correction based on the second photon count;
apply a second pile-up correction to the first photon count at each detector to obtain a corrected first photon count, the second pile-up correction based on the first pile-up correction and the corrected second photon count;
add the first corrected photon count to the second corrected photon count at each detector to obtain a total output photon count at each detector; and
reconstruct an image based on the total output photon count at each detector, and output the image to a display device of the PCCT system.

18. The PCCT system of claim 17, wherein alternately increasing the X-ray tube output current of the PCCT system above the prescribed current and decreasing the X-ray tube output current below the prescribed current further comprises increasing the X-ray tube output current to a first high current for a first duration, and decreasing the X-ray tube output current to a second low current for a second duration, the prescribed current equal to an average of the first high current and the second low current.

19. The PCCT system of claim 18, wherein the first pile-up correction is an output of a pile-up calibration model that takes as inputs the second photon count and the decreased X-ray tube output current.

20. The PCCT system of claim 19, wherein applying the second pile-up correction to the first photon count at each detector, the second pile-up correction based on the first pile-up correction further comprises:
multiplying the corrected second photon count by a proportional factor, the proportional factor is based on a ratio of the increased X-ray tube output current to the decreased X-ray tube output current.

\* \* \* \* \*